United States Patent
Shepherd, Jr.

(10) Patent No.: US 7,186,679 B2
(45) Date of Patent: Mar. 6, 2007

(54) STABILIZATION OF FRAGRANCES IN SALT MIXTURES BY DUAL ENCAPSULATION AND ENTRAPMENT

(75) Inventor: Walter B. Shepherd, Jr., Warwick, NY (US)

(73) Assignee: Hair Systems, Inc., Englishtown, NJ (US)

( * ) Notice: Subject to any disclaimer, the term of this patent is extended or adjusted under 35 U.S.C. 154(b) by 558 days.

(21) Appl. No.: 10/269,724

(22) Filed: Oct. 11, 2002

(65) Prior Publication Data
US 2003/0092600 A1    May 15, 2003

Related U.S. Application Data

(60) Provisional application No. 60/329,152, filed on Oct. 11, 2001.

(51) Int. Cl.
    *C11D 3/50*    (2006.01)
(52) U.S. Cl. ......................................... 512/4
(58) Field of Classification Search ............... 512/4
    See application file for complete search history.

(56) References Cited

U.S. PATENT DOCUMENTS

| 5,585,093 A | * | 12/1996 | Murphy | ..................... 424/65 |
| 5,614,179 A | * | 3/1997 | Murphy et al. | ............... 424/65 |
| 6,555,098 B1 | * | 4/2003 | Murphy et al. | ............... 424/65 |

* cited by examiner

*Primary Examiner*—Monique T. Cole
(74) *Attorney, Agent, or Firm*—Blank Rome LLP

(57) ABSTRACT

This invention provides a method for stabilization of a fragrance ingredient in a salt mixture, comprising the steps of encapsulating the fragrance ingredient in a first encapsulating material, which is water soluble and insoluble in a volatile organic solvent, to form a first encapsulated material; encapsulating a salt in a second encapsulating material which is dissolved in a volatile organic solvent to form a second encapsulated material, and then partially drying the second encapsulated material; mixing the first encapsulated material with the second encapsulated material before the volatile, organic solvent completely evaporates from the second encapsulated material; and removing remaining volatile organic solvent to form a free flowing salt and fragrance containing powder.

20 Claims, No Drawings

STABILIZATION OF FRAGRANCES IN SALT MIXTURES BY DUAL ENCAPSULATION AND ENTRAPMENT

RELATED APPLICATIONS

This application is a continuation of Provisional Application No. 60/329,152, filed Oct. 11, 2001.

BACKGROUND OF THE INVENTION

Fragrances used in cosmetics and personal care products increase the esthetic appeal of the product by masking or covering the base odor of the ingredients comprising the product. In most cases, the fragrances are blends of a number of natural or synthetic chemicals, which when blended together produce a characteristic aroma. The fragrance is essentially an inactive ingredient of the product, being added to enhance its esthetic appeal.

A fragrance component of a particular product may contain also one or more essential oils or chemical compounds having a claimed therapeutic effect. In such cases, the essential oils or chemical compounds reportedly produce, create or cause an emotional or physiological change when the subject inhales the aroma of the fragrance. Here, the fragrance is an active ingredient of the product, and the product for this purpose is often called "aroma therapy."

Such fragrances may be found in aqueous and non-aqueous liquid, creams, lotions, gels and pastes, as well as in powdered compositions. When fragrances are added to products of this nature, the fragrance often degrades or changes with time, and creates an undesirable odor, or, in some cases, a pronounced color change in the product containing the fragrance.

Without being bound by any theory or particular mechanism, the degradation of the fragrance is believed to be caused by chemical reaction among the various components of the fragrance and the components comprising the base product. These chemical reactions are cumulative, and are enhanced by exposure to heat, light, and sometimes the atmosphere.

The degradation of fragrances also occurs in powdered products, particularly those containing granular salts, such as sodium chloride, magnesium sulfate, sodium sesquicarbonate, and sodium bicarbonate. In such products, the fragrance is generally sprayed directly onto the surface of the salt or salts during a dry blending process.

The degradation of the fragrance in powdered products in most cases is more pronounced than in aqueous and non-aqueous liquid products. They may develop an undesirable odor or discoloration, particularly in products containing sodium chloride, whether alone or in combination with other salts having large particle sizes, i.e., greater than 20 mesh (0.85 millimeter).

Typical powdered products of this type include bath salts, body and foot soaks, body and facial masques and other cosmetic and personal care products. As noted above, these products may be simply esthetically fragranced or may be intended for use in aroma therapeutic applications.

It would therefore be desirable to provide a formulation and method of manufacture which addresses the problem of fragrance decomposition or degradation.

SUMMARY OF THE INVENTION

It has been discovered that it is possible to minimize, and in many cases totally eliminate, the degradation of the fragrance or color of a powdered composition as described above through the practice of the present invention which provides a composition and method to create a multi-component mixture in which the fragrance and color ingredients are first encapsulated and then affixed to the surface of the powdered (granular) components of the mixture which are also encapsulated or otherwise coated. The process involves a mixture created by first applying a coating material dispersed or dissolved in a volatile solvent with or without color, to the powdered (granular) component of the mixture and then adding to the powdered (granular) component a fragrance or color component that has been encapsulated in a separate process using an encapsulating material that is insoluble in the volatile solvent.

DETAILED DESCRIPTION OF THE PREFERRED EMBODIMENTS

As summarized above, the present invention comprises a method for making a stable fragrance and salt containing composition, which helps to alleviate prior problems with fragrance degradation and product discoloration. The invention also comprises a composition formed from a mixture of the salt and the fragrance components. The salt is encapsulated with a polymeric coating material which dissolves in a volatile solvent, but will not dissolve the salt. The fragrance component is encapsulated in a second, water soluble polymeric material. The encapsulated fragrance component is admixed with the coated salt component, while the latter is still tacky. Any remaining solvent is removed, thereby forming a free flowing, salt and fragrance containing powder having improved fragrance stability.

Typical solvents suitable for use in this application include but may not be limited to ethanol, methanol, propanol, isopropanol, methylene chloride or 1,1,1-trichloroethane.

Coating materials for the granular salt include but may not be limited to polyvinylpyrrolidone, polyvinylpyrrolidone co- and ter-polymers, polyvinyl alcohol, polyvinyl alcohol co- and ter-polymers and acrylate and methacrylate co- and ter-polymers.

The encapsulating materials for the fragrance component suitable for use in this application include but are not limited to Carbomers.

As a dye or pigment, any CTFA approved dye, colorant, or pigment may be used. For example, any FD & C or D & C dye or pigment listed by the CTFA may be used. It should preferably be added to the composition coating the salt.

In a broad sense, the present invention may be practiced with any combination of coating and encapsulating agents having dissimilar solubilities in a chosen solvent having a volatility sufficient to allow its total evaporation from the composition during processing as described above. The coating and the encapsulating materials should preferably be water soluble so as to permit the final product to dissolve in water, thus releasing the fragrance when the product is used.

EXAMPLE 1

A mixture of 97.35 grams of salt (sodium chloride) having a particle size greater than 20 mesh (0.85 mm) is placed in a laboratory blender, and the blender is started a low speed so as to minimize particle size degradation during the process. The salt is then sprayed with 1.50 grams of a 10.0% (by weight) ethanol solution of polyvinylpyrrilidone (PVP) and mixed at low speed until the greater portion of the ethanol has evaporated and the salt granules are slightly tacky. While continuously mixing, 2.50 grams of fragrance, microencapsulated in water soluble (ethanol insoluble) agar (approximately 25% fragrance by weight) is added to the salt and the composition is blended slowly until the balance of the ethanol has evaporated.

As the ethanol evaporates, the PVP forms a tacky coating on the salt granules and the encapsulated fragrance is affixed to the tacky coating on the surface of the salt granules. As the final portion of the ethanol evaporates the PVP coating becomes non-tacky and a dry, granularfree flowing salt is obtained.

The salt granules thus formed are uniformly coated with a continuous PVP film that is then coated with a uniform and continuous layer of microencapsulated fragrance. Thus the fragrance is attached to yet not in contact with the salt.

Several mixtures were prepared by the above process using commercially available fragrances from several commercial suppliers. In all cases the fragrances show no signs of degradation or discoloration (were stable) at room temperature for over nine months at 35° C. and were also found to be stable for over six months at 40° C.

EXAMPLE 2

The compositions from EXAMPLE 1 prepare following the same procedure but with 0.005% (by weight) of selected CTFA approved dyes added with the granular salt, i.e., a dye incorporated in the PVP coating. The same commercial fragrances were used and the stability testing was identical to that used for the uncolored samples of EXAMPLE 1.

In all cases the fragrances show no signs of fragrance degradation or color change (samples were stable) at room temperature for over nine (9) months and were also found to be stable for over 6 months at 35° C. and 40° C., respectively.

When the above compositions were prepared and fully dried, they were tested in a "use situation" by simply dissolving the finished product in tepid (30° C.) and hot (55° C.) water.

In both of the above examples the salt granules were coated with a water and ethanol soluble PVP, and the fragrances were microencapsulated with a water soluble (ethanol insoluble) agar. Accordingly, during the processing of the composition the microencapsulated fragrance will not be dissolved by the ethanol used to apply the PVP coating on the salt granules.

I claim:

1. A method for stabilization of a fragrance ingredient in a salt mixture, comprising the steps of:
   encapsulating the fragrance ingredient in a first encapsulating material, which is water soluble and insoluble in a volatile organic solvent, to form a first encapsulated material;
   encapsulating a salt in a second encapsulating material which is dissolved in the volatile organic solvent to form a second encapsulated material, and then partially drying the second encapsulated material;
   mixing the first encapsulated material with the second encapsulated material before the volatile, organic solvent completely evaporates from the second encapsulated material; and
   removing remaining volatile organic solvent to form a free flowing salt and fragrance containing powder, thereby stabilizing the fragrance ingredient.

2. A method in accordance with claim 1, wherein the first encapsulating material is a crosslinked acrylic acid copolymer, carboxymethylcellulose, carboxyethylcellulose, carboxypropylcellulose, hydroxyethylcellulose, hydroxymethylcellulose, hydroxypropylcellulose, agar, gelatin, guar gum or its derivatives, xanthan gums, algin and alginates.

3. A method in accordance with claim 1, wherein the first encapsulating material is a polysaccharide.

4. A method in accordance with claim 1, wherein the second encapsulating material is polyvinylpyrrolidone, polyvinylpyrrolidone co- and ter-polymers, polyvinyl alcohol, polyvinyl alcohol co- and ter-polymers, and acrylate and methacrylate co- and ter-polymers.

5. A method in accordance with claim 1, wherein the volatile organic solvent is methanol, ethanol, propanol, isopropanol, methylene chloride, or 1,1,1-trichloromethane.

6. A method in accordance with claim 1, wherein the first encapsulating material is a water soluble, alcohol insoluble polymer, the solvent for the first encapsulating material is water, the second encapsulating material is polyvinyl pyrrolidone or a copolymer thereof, and the solvent for the second encapsulating material is an alcohol.

7. A method in accordance with claim 1, wherein the second encapsulating material is an alcohol and water soluble polyvinylpyrrolidone polymer.

8. A method in accordance with claim 7, wherein the second encapsulating material further includes a dye or pigment.

9. A method in accordance with claim 7, wherein the second encapsulating material is agar or a derivative thereof.

10. A composition which comprises a powdered or granular admixture of a salt and a fragrance ingredient; the salt encapsulated with a first material, which is soluble in a volatile organic solvent; and the fragrance encapsulated with a water soluble second material, which is insoluble in the volatile organic solvent.

11. A composition in accordance with claim 10, wherein the second material is a cross-linked acrylic acid copolymer, carboxymethylcellulose, carboxyethylcellulose, carboxypropylcellulose, hydroxyethylcellulose, hydroxymethylcellulose, hydroxypropylcellulose, agar, gelatin, guar gum or its derivatives, xanthan gums, algin and alginates.

12. A composition in accordance with claim 10, wherein the second material is a polysaccharide.

13. A composition in accordance with claim 10, wherein the first material is polyvinylpyrrolidone, polyvinylpyrrolidone co- and ter-polymers, polyvinyl alcohol, polyvinyl alcohol co- and ter-polymers, and acrylate and methacrylate co- and ter-polymers.

14. A composition in accordance with claim 13, wherein the volatile organic solvent is methanol, ethanol, propanol, isopropanol, methylene chloride, or 1,1,1-trichloromethane.

15. A composition in accordance with claim 10, wherein the second material is a water soluble, alcohol insoluble polymer, and the solvent for the first coating material is an alcohol.

16. A composition in accordance with claim 11, wherein the first material is an alcohol and water soluble polyvinylpyrrolidone polymer.

17. A composition in accordance with claim 16, wherein the first material further includes a dye or pigment.

18. A composition in accordance with claim 16, wherein the second material is crosslinked acrylic acid copolymers, carboxymethylcellulose, carboxyethylcellulose, carboxypropylcellulose, hydroxyethylcellulose, hydroxymethylcellulose, hydroxypropylcellulose, agar, gelatin, guar gum, derivatized guar gums, xanthan gums, algin and alginates or other polysaccharides.

19. A composition in accordance with claim 10, wherein the fragrance is encapsulated with the second material and admixed with the salt after encapsulating the salt with the first material before the first material is dried.

20. A method for stabilization of a fragrance in a salt mixture, comprising the steps of:

encapsulating the fragrance ingredient with an encapsulating material which is insoluble in a volatile organic solvent to form a first encapsulated material;

encapsulating the salt in a second encapsulating material which is soluble in the volatile organic solvent to form a second encapsulated material, and then partially drying the second encapsulated material;

mixing the first encapsulated material with the second encapsulated material before the second encapsulated material is completely dried; and removing remaining volatile organic to form a free flowing salt and fragrance containing powder, thereby stabilizing the fragrance ingredient.

* * * * *